United States Patent
Hashino et al.

(10) Patent No.: US 9,375,356 B2
(45) Date of Patent: Jun. 28, 2016

(54) ABSORBENT ARTICLE

(71) Applicant: UNICHARM CORPORATION, Shikokuchuo-shi, Ehime (JP)

(72) Inventors: Akira Hashino, Kanonji (JP); Yuki Noda, Kanonji (JP); Tatsuya Tamura, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 0 days.

(21) Appl. No.: 14/390,007

(22) PCT Filed: Mar. 26, 2013

(86) PCT No.: PCT/JP2013/058861
§ 371 (c)(1),
(2) Date: Oct. 1, 2014

(87) PCT Pub. No.: WO2013/150923
PCT Pub. Date: Oct. 10, 2013

(65) Prior Publication Data
US 2015/0094683 A1 Apr. 2, 2015

(30) Foreign Application Priority Data

Apr. 2, 2012 (JP) ................................. 2012-084287

(51) Int. Cl.
*A61F 13/15* (2006.01)
*A61F 13/47* (2006.01)
(Continued)

(52) U.S. Cl.
CPC ........... *A61F 13/4704* (2013.01); *A61F 13/472* (2013.01); *A61F 13/512* (2013.01);
(Continued)

(58) Field of Classification Search
CPC . A61F 13/52; A61F 13/511; A61F 13/51104; A61F 13/51113; A61F 13/513; A61F 2013/51066; A61F 2013/51061; A61F 2013/51059

USPC ............... 604/367, 364, 378, 381, 382
See application file for complete search history.

(56) References Cited

U.S. PATENT DOCUMENTS 3,929,135 A 12/1975 Thompson
4,263,363 A * 4/1981 Buck ..................... A61L 15/20
428/318.8

(Continued)

FOREIGN PATENT DOCUMENTS

CN 1432352 A 7/2003
EP 1250940 A1 10/2002
(Continued)

OTHER PUBLICATIONS

Atsushi Fujita, "Prediction of Organic Compounds and Organic Conceptual Diagram", Kagaku no Ryoiki (Region of Chemistry), Oct. 1957, p. 719-725, vol. 11, No. 10.
(Continued)

*Primary Examiner* — Jacqueline Stephens
(74) *Attorney, Agent, or Firm* — Hauptman Ham, LLP

(57) ABSTRACT

The objective of the present disclosure is to provide an absorbent article that enables the rapid transfer of menstrual blood to an absorbent body, is not susceptible to the spread of menstrual blood above a top sheet, and is not susceptible to causing feelings of stickiness on the top sheet. The absorbent article of the present disclosure has the following structure. An absorbent article (1) having a liquid-permeable top sheet (2), a liquid-impermeable back sheet, and an absorbent body (3). The absorbent article (1) is characterized by: having an excretory orifice contact region (4) and embossed portions (5); the top sheet (2) inside the excretory orifice contact region (4) and the embossed portions (5) respectively containing a prescribed blood lubricating agent; and the amount of the blood lubricating agent in the embossed portions (5) being larger than the amount of the blood lubricating agent in the top sheet (2) in the excretory orifice contact region (4).

14 Claims, 4 Drawing Sheets

(51) Int. Cl.
*A61F 13/472* (2006.01)
*A61F 13/512* (2006.01)
*A61F 13/511* (2006.01)
*A61F 13/51* (2006.01)

(52) U.S. Cl.
CPC ......... *A61F13/51113* (2013.01); *A61F 13/511* (2013.01); *A61F 13/51104* (2013.01); *A61F 13/52* (2013.01); *A61F 2013/4708* (2013.01); *A61F 2013/51059* (2013.01); *A61F 2013/51061* (2013.01); *A61F 2013/51066* (2013.01)

(56) References Cited

U.S. PATENT DOCUMENTS

| | | | |
|---|---|---|---|
| 4,588,630 | A | 5/1986 | Shimalla |
| 4,759,754 | A | 7/1988 | Korpman |
| 5,078,710 | A | 1/1992 | Suda et al. |
| 5,334,176 | A | 8/1994 | Buenger et al. |
| 5,344,416 | A | 9/1994 | Niihara |
| 5,614,283 | A | 3/1997 | Potnis et al. |
| 5,650,214 | A | 7/1997 | Anderson et al. |
| 5,693,037 | A * | 12/1997 | Lee ................ A61F 13/512 604/378 |
| 6,153,209 | A | 11/2000 | Vega et al. |
| 6,730,819 | B1 | 5/2004 | Pesce |
| 2001/0029141 | A1 | 10/2001 | Mizutani et al. |
| 2003/0088222 | A1 | 5/2003 | Yoshimasa et al. |
| 2003/0149410 | A1 | 8/2003 | Kudo et al. |
| 2003/0198784 | A1 | 10/2003 | Mizutani et al. |
| 2006/0184150 | A1* | 8/2006 | Noel ................ A61F 13/15203 604/383 |
| 2006/0276767 | A1 | 12/2006 | Ueminami et al. |
| 2007/0219515 | A1 | 9/2007 | Marsh et al. |
| 2007/0298213 | A1 | 12/2007 | Noda et al. |
| 2007/0298214 | A1 | 12/2007 | Noda et al. |
| 2007/0298220 | A1 | 12/2007 | Noda et al. |
| 2007/0298667 | A1 | 12/2007 | Noda et al. |
| 2007/0298671 | A1 | 12/2007 | Noda et al. |
| 2007/0299416 | A1 | 12/2007 | Noda et al. |
| 2008/0010795 | A1 | 1/2008 | Mizutani et al. |
| 2008/0044622 | A1 | 2/2008 | Noda et al. |
| 2008/0044628 | A1 | 2/2008 | Noda et al. |
| 2008/0045915 | A1 | 2/2008 | Noda et al. |
| 2008/0085399 | A1 | 4/2008 | Noda et al. |
| 2008/0132136 | A1 | 6/2008 | Uematsu et al. |
| 2008/0200894 | A1 | 8/2008 | Gatto et al. |
| 2009/0221978 | A1 | 9/2009 | Gatto et al. |
| 2009/0282660 | A1 | 11/2009 | Noda et al. |
| 2010/0069874 | A1 | 3/2010 | Noda et al. |
| 2010/0137824 | A1 | 6/2010 | Uematsu et al. |
| 2010/0191207 | A1 | 7/2010 | Oba et al. |
| 2011/0319851 | A1* | 12/2011 | Kudo ................ A61F 13/4704 604/380 |
| 2012/0045620 | A1 | 2/2012 | Oba et al. |
| 2012/0141742 | A1 | 6/2012 | Yamaguchi et al. |
| 2012/0177889 | A1 | 7/2012 | Uematsu et al. |
| 2012/0196091 | A1 | 8/2012 | Mizutani et al. |
| 2013/0034686 | A1 | 2/2013 | Mitsuno |
| 2013/0137328 | A1 | 5/2013 | Mitsuno |
| 2013/0226123 | A1 | 8/2013 | Kudo et al. |

FOREIGN PATENT DOCUMENTS

| | | |
|---|---|---|
| EP | 1362568 A2 | 11/2003 |
| EP | 1371379 A1 | 12/2003 |
| EP | 2036521 A1 | 3/2009 |
| EP | 2433602 A1 | 3/2012 |
| EP | 2821037 A1 | 1/2015 |
| EP | 2821041 A1 | 1/2015 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | 02152920 A | 6/1990 |
| JP | H02-229255 | 9/1990 |
| JP | H05-154176 | 6/1993 |
| JP | H06-5614 U | 1/1994 |
| JP | 6502104 A | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 A | 10/1998 |
| JP | H11-512643 | 11/1999 |
| JP | 2000-510376 | 8/2000 |
| JP | 3091283 | 9/2000 |
| JP | 2000-512886 A | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002528174 A | 9/2002 |
| JP | 2002537904 A | 11/2002 |
| JP | 200324372 A | 1/2003 |
| JP | 200352750 A | 2/2003 |
| JP | 2004-500908 | 1/2004 |
| JP | 200449529 A | 2/2004 |
| JP | 2005-504591 A | 2/2005 |
| JP | 2005-095759 | 4/2005 |
| JP | 2005193001 A | 7/2005 |
| JP | 2005-525134 A | 8/2005 |
| JP | 2006501022 A | 1/2006 |
| JP | 2006-510456 | 3/2006 |
| JP | 2006115996 A | 5/2006 |
| JP | 2006-255051 | 9/2006 |
| JP | 2006280526 A | 10/2006 |
| JP | 200714705 A | 1/2007 |
| JP | 2007-509695 A | 4/2007 |
| JP | 2008-002034 A | 1/2008 |
| JP | 2008-023311 A | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 A | 2/2008 |
| JP | 2008-025085 A | 2/2008 |
| JP | 2008-503323 A | 2/2008 |
| JP | 200823365 A | 2/2008 |
| JP | 200825078 A | 2/2008 |
| JP | 200825079 A | 2/2008 |
| JP | 200829830 A | 2/2008 |
| JP | 2008-138340 A | 6/2008 |
| JP | 2008-144322 A | 6/2008 |
| JP | 2008-529721 A | 8/2008 |
| JP | 2008229032 A | 10/2008 |
| JP | 2008229033 A | 10/2008 |
| JP | 2008237569 A | 10/2008 |
| JP | 2008-264084 A | 11/2008 |
| JP | 2008-266813 A | 11/2008 |
| JP | 2008-541943 A | 11/2008 |
| JP | 2008-307179 | 12/2008 |
| JP | 20095767 A | 1/2009 |
| JP | 2009-030218 A | 2/2009 |
| JP | 2009-201878 | 9/2009 |
| JP | 2009297048 A | 12/2009 |
| JP | 201088822 A | 4/2010 |
| JP | 2010-518918 A | 6/2010 |
| JP | 2010518918 A | 6/2010 |
| JP | 2010-148708 A | 7/2010 |
| JP | 2010526629 A | 8/2010 |
| JP | 2010-285735 | 12/2010 |
| JP | 2010279568 A | 12/2010 |
| JP | 2011-038211 | 2/2011 |
| JP | 2011-074515 A | 4/2011 |
| JP | 2011-080178 | 4/2011 |
| JP | 201167484 A | 4/2011 |
| JP | 201172650 A | 4/2011 |
| JP | 2011510801 A | 4/2011 |
| JP | 4693847 B2 | 6/2011 |
| JP | 2011104001 A | 6/2011 |
| JP | 2011104059 A | 6/2011 |

(56) References Cited

FOREIGN PATENT DOCUMENTS

| | | |
|---|---|---|
| JP | 2011120696 A | 6/2011 |
| JP | 2011226010 A | 11/2011 |
| JP | 2011226011 A | 11/2011 |
| JP | 2012-50626 A | 3/2012 |
| JP | 5122007 B1 | 1/2013 |
| WO | 9301781 A1 | 2/1993 |
| WO | 94/27539 | 12/1994 |
| WO | 96/19173 A1 | 6/1996 |
| WO | 98/55158 A2 | 12/1998 |
| WO | 99/00093 | 1/1999 |
| WO | 99/29274 | 6/1999 |
| WO | 0024351 A1 | 5/2000 |
| WO | 01/45757 | 6/2001 |
| WO | 03/017900 A1 | 3/2003 |
| WO | 03/028776 A1 | 4/2003 |
| WO | 2004030713 A1 | 4/2004 |
| WO | 2004/058119 | 7/2004 |
| WO | 2005/044164 A1 | 5/2005 |
| WO | 2006/009996 A1 | 1/2006 |
| WO | 2006/130646 A1 | 12/2006 |
| WO | 2008072675 A1 | 6/2008 |
| WO | 2008101163 A2 | 8/2008 |
| WO | 2008139425 A1 | 11/2008 |
| WO | 2008-149771 | 12/2008 |
| WO | 2009102837 A2 | 8/2009 |
| WO | 2012/133724 A1 | 10/2012 |
| WO | 2013/047867 A1 | 4/2013 |

OTHER PUBLICATIONS

International Search Report mailed Jul. 3, 2012 in corresponding International Application No. PCT/JP2012/058499.
International Search Report mailed Mar. 19, 2013 in corresponding International Application No. PCT/JP2012/082087.
International Search Report mailed Mar. 12, 2013 in corresponding International Application No. PCT/JP2012/082104.
International Search Report mailed Mar. 19, 2013 in corresponding International Application No. PCT/JP2013/054382.
International International Search Report mailed May 21, 2014 in corresponding International Application No. PCT/JP2013/054796.
International Search Report mailed Mar. 26, 2013, corresponds to International Application No. PCT/JP2012/082977.
International Search Report mailed Jan. 8, 2013, corresponds to International Application No. PCT/JP2012/075583.
International Search Report mailed Jul. 17, 2012, corresponds to International Application No. PCT/JP2012/061505.
Corresponding International Application No. PCT/JP2012/058499 Written Opinion dated Jul. 3, 2012.
Corresponding International Application No. PCT/JP2012/058499 Reply to Written Opinion dated Jan. 30, 2013.
International Search Report mailed May 21, 2013, corresponds to International Application No. PCT/JP2013/058859.
International Search Report mailed Jun. 18, 2013, corresponds to International Application No. PCT/JP2013/058855.
International Search Report mailed Jul. 2, 2013, corresponds to International Application No. PCT/JP2013/058860.
International Search Report mailed Jul. 2, 2013, corresponds to International Application No. PCT/JP2013/058862.
International Search Report mailed Jul. 2, 2013, corresponds to International Application No. PCT/JP2013/058861.
International Search Report mailed May 14, 2013, corresponds to International Application No. PCT/JP2013/058836.

* cited by examiner

200 μm (a)

50 μm (b)

50 μm

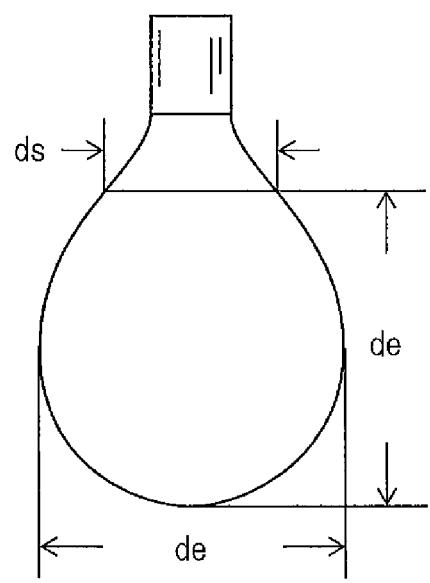

ABSORBENT ARTICLE

CROSS-REFERENCES TO RELATED APPLICATIONS

The present application is a National Phase of International Application Number PCT/JP2013/058861 filed Mar. 26, 2013, which claims the priority of Japanese patent Application No. 2012-084287 filed Apr. 2, 2012.

TECHNICAL FIELD

The present disclosure relates to an absorbent article.

BACKGROUND ART

As the basic performance of absorbent articles, such as sanitary napkins and panty liners has continued to improve with technological development over many years, leakage after absorption of excreta, such as menstrual blood has become a less frequent occurrence than in the past, and research is currently ongoing with the aim of achieving even higher performance, including a feel similar to underwear, and smoothness of the top sheet even after absorption of excreta, such as menstrual blood.

Menstrual blood during menstruation, in particular, can also contain components of the endometrium which are highly viscous, and the top sheet preferably remains smooth and stick-free even after absorption of such highly viscous menstrual blood. Highly viscous menstrual blood usually remains on the top sheet in the form of masses, generally leaving the user with a visually unpleasant image, and therefore from this viewpoint as well it is preferred for no highly viscous menstrual blood to remain on the top sheet.

For example, PTL 1 discloses an absorbent article having a polypropylene glycol material-containing lotion composition situated on the inner surface of the top sheet (the clothing side surface), the inner surface of the back sheet (the body side surface), and on the base material between the inner surface of the top sheet and the inner surface of the back sheet.

Also, PTL 2 discloses an absorbent article wherein a polypropylene glycol material-containing lotion composition is applied on the outer surface of the top sheet (body side surface).

CITATION LIST

Patent Literature

PTL 1 Japanese Unexamined Patent Publication No. 2010-518918
PTL 2 Japanese Unexamined Patent Publication No. 2011-510801

SUMMARY OF INVENTION

Technical Problem

In a top sheet made of a nonwoven fabric or woven fabric, the absorbed menstrual blood tends to collect by capillary movement in the regions of high fiber density, and the collected menstrual blood often contacts with the skin of the wearer, causing the wearer to feel discomfort. The absorbent articles described in PTLs 1 and 2 are not designed so that absorbed menstrual blood moves into the absorbent body without collecting in the regions of high fiber density.

It is therefore an object of the present disclosure to provide an absorbent article that allows menstrual blood to rapidly migrate into the absorbent body and minimizes diffusion of menstrual blood on the top sheet, and that has reduced stickiness on the top sheet and maintains smoothness on the top sheet, after absorption of menstrual blood.

Solution to Problems

As a result of diligent research directed toward solving the problems described above, the present inventors have discovered an absorbent article comprising a liquid-permeable top sheet, formed from a nonwoven fabric or woven fabric, a liquid-impermeable back sheet, and an absorbent body between the top sheet and the back sheet, wherein the absorbent article has an excretory opening contact region that contacts with the excretory opening of the wearer, and an embossed section which is continuously or discontinuously disposed and which surrounds the excretory opening contact region, the embossed section is formed by embossing the layer comprising the top sheet and the absorbent body, the top sheet within the excretory opening contact region and the embossed section contain a blood slipping agent that has a kinematic viscosity of 0.01 to 80 mm$^2$/s at 40° C., a water holding percentage of 0.01 to 4.0 mass % and a weight-average molecular weight of less than 1000, and the basis weight of the blood slipping agent in the embossed section is greater than the basis weight of blood slipping agent in the top sheet within the excretory opening contact region.

Advantageous Effects of Invention

The absorbent article of the present disclosure allows menstrual blood to rapidly migrate into the absorbent body and minimizes diffusion of menstrual blood on the top sheet, while also having reduced stickiness on the top sheet and maintaining smoothness on the top sheet, after absorption of menstrual blood.

BRIEF DESCRIPTION OF DRAWINGS

FIG. 5 is a diagram illustrating a method of measuring surface tension.

DESCRIPTION OF EMBODIMENTS

Figure 1:
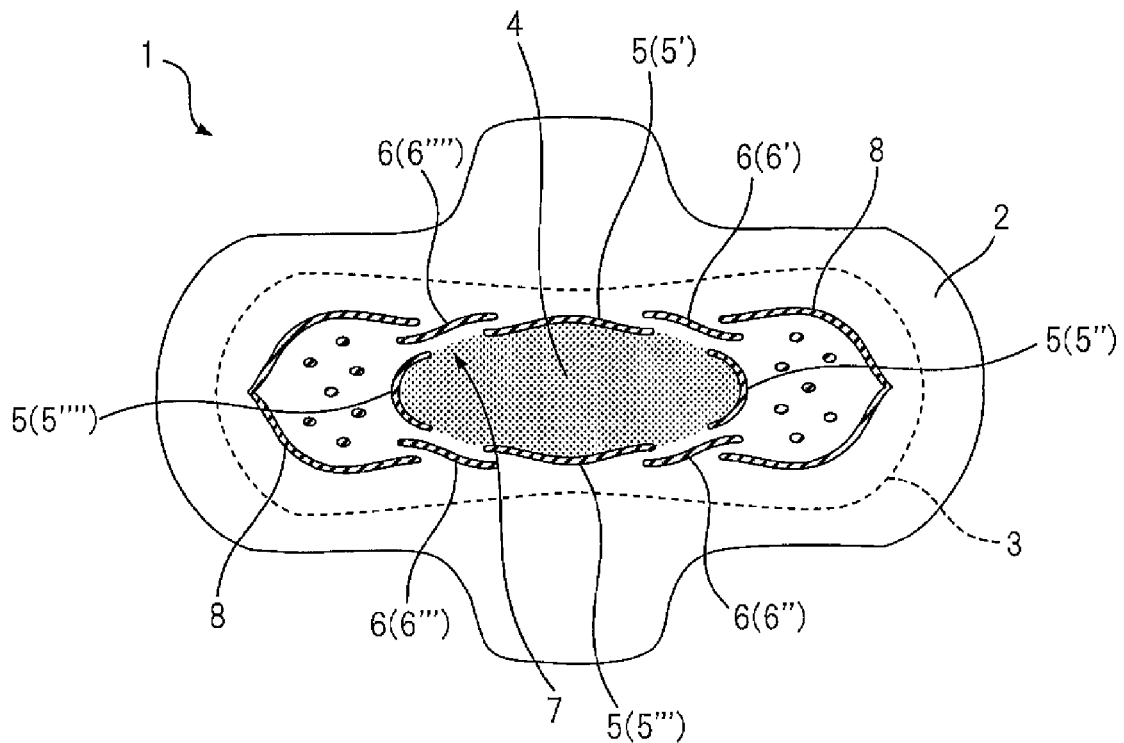
FIG. 1 is a front view of a sanitary napkin according to an embodiment of the absorbent article of the present disclosure.

The absorbent article of the present disclosure will now be explained in detail.
FIG. 1 is a front view of a sanitary napkin according to an embodiment of the absorbent article of the present disclosure. FIG. 1 is as observed from the skin contact side of the top sheet 2. The sanitary napkin 1 shown in FIG. 1 has a liquid-permeable top sheet 2, a liquid-impermeable back sheet (not shown), and an absorbent body 3 between the top sheet 2 and the back sheet. In FIG. 1, the top sheet 2 is formed from a nonwoven fabric.

The sanitary napkin 1 shown in FIG. 1 has an excretory opening contact region 4 that contacts with the excretory opening of a wearer, and embossed sections 5', 5", 5'" and 5"" (total of four, hereunder also referred to as "embossed section 5") which is discontinuously disposed so as to surround the excretory opening contact region 4. The embossed sections 5', 5", 5'" and 5"" are each independently disposed surrounding the excretory opening contact region 4.

The embossed section 5 is formed by embossing the layer comprising the top sheet 2 and the absorbent body 3.

As used herein, the term "excretory opening contact region" means the region that contacts with the excretory opening (e.g. labia minora) of the wearer, and it is defined by an embossed section which is continuously or discontinuously disposed. The excretory opening contact region will have a different location depending on the size of the absorbent article, and for an absorbent article without wing sections, for example, the excretory opening contact region is the interior area of the region defined by the embossed section which is continuously or discontinuously disposed so as to surround the widthwise center section and lengthwise center section of the absorbent article. When the absorbent article has wing sections, for example, the excretory opening contact region is the interior area of the region defined by the embossed section which is continuously or discontinuously disposed so as to surround the intersection between a line in the lengthwise direction that passes through the widthwise center of the absorbent article, and a line in the widthwise direction that passes through the lengthwise center of both wing sections.

In the sanitary napkin 1 shown in FIG. 1, the top sheet 2 within the excretory opening contact region 4 and the embossed section 5 each comprise the blood slipping agent described hereunder, the basis weight of the blood slipping agent in the embossed section 5 being greater than the basis weight of the blood slipping agent in the top sheet 2 within the excretory opening contact region 4. The blood slipping agent is not shown in FIG. 1.

The sanitary napkin shown in FIG. 1 also has four additional embossed sections 6', 6", 6'" and 6"" (hereunder also referred to as "embossed section 6"), on the outer side of the embossed section 5. The embossed sections 6', 6", 6'" and 6"" are disposed on the outer side of the discontinuous sections 7 of the embossed section 5. In the sanitary napkin 1 shown in FIG. 1, the embossed section 6 contains a blood slipping agent, and the basis weight of the blood slipping agent in the embossed section 6 is greater than the basis weight of the blood slipping agent in the top sheet 2 within the excretory opening contact region 4.

The sanitary napkin 1 shown in FIG. 1 also has second embossed sections 8 disposed on the outer side of the excretory opening contact region 4 in the lengthwise direction, and formed by embossing the layer comprising the top sheet 2 and the absorbent body 3. In the sanitary napkin 1 shown in FIG. 1, the second embossed sections 8 are disposed in a curved manner so as to surround the edges of the excretory opening contact region 4 in the lengthwise direction.

The function of the absorbent article of the present disclosure will now be explained with reference to FIG. 1.

Highly viscous menstrual blood first reaches the excretory opening contact region 4 of the top sheet 2 of the sanitary napkin 1. Since the top sheet 2 in the excretory opening contact region 4 contains a blood slipping agent, the menstrual blood migrates into the sanitary napkin 1 together with the blood slipping agent, and rapidly migrates into the absorbent body 3.

Thus, the sanitary napkin 1 allows rapid migration of absorbed menstrual blood into the absorbent body 3.

It is generally known that when a wearer is lying down during sleep, menstrual blood that has reached the excretory opening contact region of the top sheet often flows out of the excretory opening contact region along the skin contact surface. In the sanitary napkin 1 shown in FIG. 1, however, the embossed section 5 surrounding the excretory opening contact region 4 has more blood slipping agent than the top sheet 2 within the excretory opening contact region 4, the blood slipping agent in the embossed section 5 repels menstrual blood attempting to flow out of the excretory opening contact region 4, pushing the menstrual blood back into the excretory opening contact region 4. The menstrual blood that has been pushed back migrates into the sanitary napkin 1 together with the blood slipping agent of the excretory opening contact region 4, and migrates into the absorbent body 3.

In many cases, as well, menstrual blood that has reached the sanitary napkin may diffuse to the outer side of the excretory opening contact region inside the top sheet. In the sanitary napkin 1 shown in FIG. 1, however, since the embossed section 5 surrounding the excretory opening contact region 4 has more blood slipping agent than the top sheet 2 within the excretory opening contact region 4, menstrual blood attempting to diffuse to the outer side of the excretory opening contact region 4 in the top sheet 2 is blocked by the embossed section 5, and either is repelled into the top sheet 2 within the excretory opening contact region 4, or caused to migrate into the absorbent body 3.

Thus, the sanitary napkin 1 minimizes diffusion of absorbed menstrual blood on the top sheet, and reduces leakage of menstrual blood.

As shown in FIG. 1, the embossed section surrounding the excretory opening contact region in the absorbent article may be discontinuously disposed in order to avoid resulting in a hard absorbent article.

Since the sanitary napkin 1 shown in FIG. 1 has additional embossed section 6 (embossed sections 6', 6", 6'" and 6"") disposed on the outer side of the discontinuous sections 7 of the embossed section 5 surrounding the excretory opening contact region 4, menstrual blood attempting to diffuse through the discontinuous sections 7 is blocked by the additional embossed section 6, and is repelled into the excretory opening contact region 4. This function is increased if the additional embossed section 6 contains a blood slipping agent.

According to another embodiment of the absorbent article of the present disclosure, one or more additional embossed sections are further disposed on the outer side of the embossed sections in the absorbent article, and the one or more embossed sections do not contain a blood slipping agent.

The sanitary napkin 1 shown in FIG. 1 includes second embossed sections 8 disposed on the outer side of the excretory opening contact region 4 in the lengthwise direction, and the presence of the second embossed sections 8 provides the following advantages.

As mentioned above, menstrual blood migrates into the sanitary napkin 1 together with the blood slipping agent of the top sheet 2 within the excretory opening contact region 4, and rapidly migrates to and into the absorbent body 3. Then, as time passes, the menstrual blood and blood slipping agent that have migrated into the absorbent body 3 begin to migrate toward the outer sides of the absorbent body, such as toward the outer sides of the absorbent body in the lengthwise direction. Since the menstrual blood is present with the blood slipping agent, migration within the absorbent body is also facilitated.

When menstrual blood that has begun to migrate toward the outer side of the absorbent body in the lengthwise direction reaches the edges of the absorbent body in the lengthwise direction, the menstrual blood will sometimes tend to leak, but the second embossed sections 8 disposed on the outer sides of the excretory opening contact region 4 in the lengthwise direction block the menstrual blood and can repel it in the direction of the excretory opening contact region, thereby minimizing leakage of menstrual blood.

In the sanitary napkin 1 shown in FIG. 1, the second embossed sections 8 are disposed in a curved manner so as to surround the edges of the excretory opening contact region 4 in the lengthwise direction, thus allowing effective blockage of menstrual blood.

The shapes of the second embossing sections in the absorbent article of the present disclosure are not particularly restricted, and for example, they may have roughly U-shaped, roughly V-shaped, roughly Y-shaped, roughly circular arc-shaped or roughly elliptical arc-shaped forms.

In the sanitary napkin 1 shown in FIG. 1, a total of two second embossed sections 8 are disposed on the outer sides of the excretory opening contact region 4 in the lengthwise direction, but according to another embodiment of the absorbent article of the present disclosure, only one second embossed section may be disposed on the outer sides of the excretory opening contact region in the lengthwise direction, situated toward the rear for wearers more prone to leakage.

In the sanitary napkin 1 shown in FIG. 1, the top sheet 2 within the excretory opening contact region 4 contains a blood slipping agent over the entire planar direction, but according to another embodiment of the absorbent article of the present disclosure, it contains a blood slipping agent only over part of the planar direction of the top sheet within the excretory opening contact region.

Figure 2:
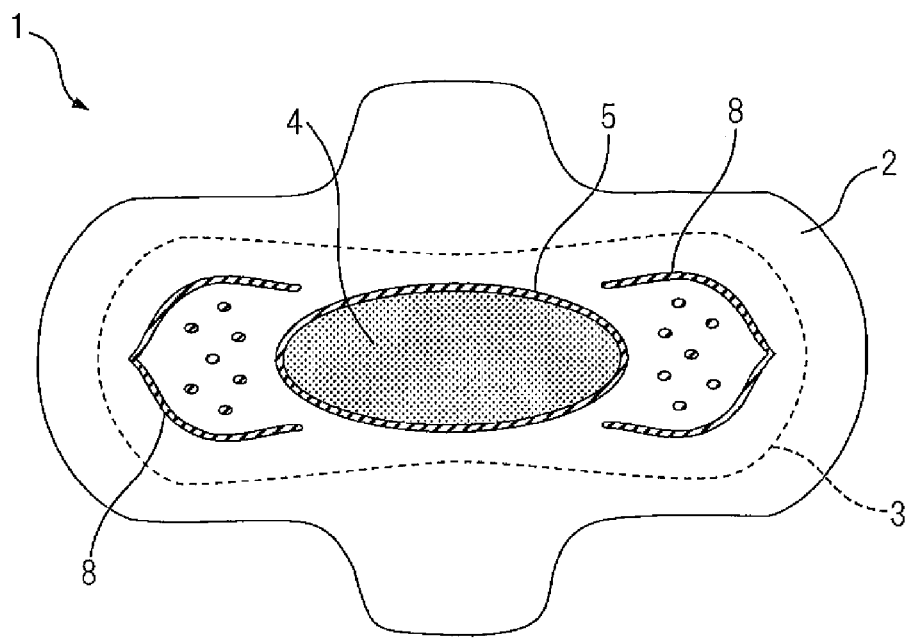
FIG. 2 is a front view of a sanitary napkin according to another embodiment of the absorbent article of the present disclosure.

FIG. 2 is a front view of a sanitary napkin, according to another embodiment of the absorbent article of the present disclosure. The sanitary napkin 1 shown in FIG. 2 differs from the sanitary napkin 1 shown in FIG. 1 in that the embossed section 5 is continuously disposed so as to surround the excretory opening contact region 4, and no additional embossed section is present, but it is otherwise identical to the sanitary napkin 1 shown in FIG. 1.

If the embossed section 5 is continuously disposed so as to surround the excretory opening contact region 4, as shown in FIG. 2, menstrual blood that attempts to diffuse out of the excretory opening contact region 4 along the skin contact surface of the top sheet 2 or through the interior of the top sheet 2, will be blocked by the embossed section 5, and can either be repelled into the top sheet 2 within the excretory opening contact region 4, or caused to migrate into the absorbent body 3.

In the embodiments shown in FIG. 1 and FIG. 2, the absorbent article has a liquid-permeable top sheet, a liquid-impermeable back sheet and an absorbent body between the top sheet and back sheet, but according to another embodiment of the absorbent article of the present disclosure, the absorbent article may also include a second sheet. That is, for those embodiments the absorbent article has the liquid-impermeable back sheet, absorbent body, second sheet and liquid-permeable top sheet in that order.

Also, the embossed section for these embodiments may be formed by embossing the layer comprising the top sheet, second sheet and absorbent body.

As used herein, the simple term "embossed section" refers to an embossed section which is continuously or discontinuously disposed so as to surround the excretory opening contact region.

In the absorbent article of the present disclosure, the amount of blood slipping agent in the embossed section is greater than the amount of blood slipping agent in the top sheet within the excretory opening contact region, and the basis weight of the blood slipping agent in the embossed section is preferably about 0.01 to about 20 $g/m^2$ and more preferably about 0.1 to about 10 $g/m^2$ higher than the basis weight of the blood slipping agent in the top sheet within the excretory opening contact region. If the difference in basis weights is less than about 0.01 $g/m^2$, it may be difficult for menstrual blood that has reached the embossed section to be repelled into the excretory opening contact region. If the difference in basis weights is greater than about 20 $g/m^2$, either the amount of blood slipping agent in the embossed section will be greater, increasing the feeling of wetness during wear, or the amount of blood slipping agent in the top sheet within the excretory opening contact region will be lower, making it difficult for the blood slipping agent to act on menstrual blood that has reached the excretory opening contact region.

The basis weight of the blood slipping agent in the embossed section is preferably about 1 to about 30 $g/m^2$, more preferably about 2 to about 20 $g/m^2$ and even more preferably about 3 to about 10 $g/m^2$. If basis weight is less than about 1 $g/m^2$, it may be difficult for menstrual blood that has reached the embossed section to be repelled into the excretory opening contact region, while if the basis weight is greater than about 30 $g/m^2$, the feeling of wetness during wear will tend to be increased.

In an embodiment in which the absorbent article of the present disclosure comprises one or more additional embossed sections and the one or more additional embossed sections contain a blood modifying agent, the range for the amount of blood slipping agent to be contained in the additional embossed sections is the same as the range for the embossed section.

The amount of blood slipping agent in the embossed section, the amount of blood slipping agent in the top sheet within the excretory opening contact region and the amount of blood slipping agent in the optional additional embossed sections (for example, the basis weight), may be measured, for example, by cutting out a sample to be measured, measuring the flat area and weight, and then dipping it in a solvent to dissolve the blood slipping agent, and determining the amount of the separated blood slipping agent from the mass of the dipped sample. The solvent may be, for example, a ketone-based solvent, such as acetone, an alcohol-based solvent, such as ethanol, or an aromatic solvent, such as toluene.

In the embodiment shown in FIG. 1, the top sheet 2 within the excretory opening contact region 4, the embossed section 5 and the additional embossed section 6 contain a blood slipping agent, while the top sheet on the outer side of the additional embossed section 6 does not contain a blood slipping agent, but according to another embodiment of the absorbent article of the present disclosure, the top sheet outside of the additional embossed section includes embossed sections.

In the embodiment shown in FIG. 2, the top sheet 2 within the excretory opening contact region 4 and the embossed section 5 contain a blood slipping agent, while the top sheet on the outer side of the embossed section 5 does not contain a blood slipping agent, but according to another embodiment of the absorbent article of the present disclosure, the top sheet outside of the embossed section includes embossed sections.

As used herein, the size of the "excretory opening contact region" differs depending on the size of the absorbent article itself, and for example, it may be a length of about 50 to about 180 mm or about 80 to about 120 mm in the lengthwise direction of the absorbent article, and a length of about 10 to about 60 mm or about 20 to about 40 mm in the widthwise direction of the absorbent article.

According to one embodiment of the absorbent article of the present disclosure, the absorbent article has an embossed section formed by embossing the layer comprising the top sheet and absorbent body in the excretory opening contact region. By having embossed section in the excretory opening contact region, highly viscous menstrual blood will slide into the recesses formed by the embossed section, temporarily separating it from the skin.

Also, according to an embodiment of the absorbent article of the present disclosure, the absorbent article has an embossed section formed by embossing the layer comprising the top sheet and absorbent body, on the outer side of the embossed section which is continuously or discontinuously disposed so as to surround the excretory opening contact region, and more preferably, on the outer side of the absorbent article in the lengthwise direction.

Since the blood slipping agent has a kinematic viscosity of about 0.01 to about 80 mm$^2$/s at 40° C., it has very low viscosity near the body temperature of the wearer, and since it has a water holding percentage of about 0.01 to about 4.0 mass %, it exhibits constant affinity with menstrual blood and migrates together with menstrual blood into the absorbent body.

In addition, if the blood slipping agent has a hydrophobic portion composed of a hydrocarbon portion, and a hydrophilic portion composed of a hydrophilic group (a polar group, such as carbonyl, oxy, carboxyl or hydroxyl), a hydrophilic bond (a polar bond, such as a carbonyl bond, ester bond, carbonate bond or ether bond) or the like, the blood slipping agent will have an effect of facilitating sliding of menstrual blood.

The hydrophobic portion of the blood slipping agent repels the hydrophilic components in menstrual blood (such as blood plasma) while the hydrophilic portion of the blood slipping agent attracts the hydrophilic components in menstrual blood (such as blood plasma), and therefore menstrual blood will easily slide into the absorbent body.

In addition, since the blood slipping agent has a water holding percentage of about 0.01 to about 4.0 mass % and its affinity with the hydrophilic components (such as blood plasma) in menstrual blood is not excessively high, less of the menstrual blood remains on the top sheet.

Furthermore, since the blood slipping agent has a water holding percentage of about 0.01 to about 4.0 mass % and optionally an IOB of about 0.00 to about 0.60, its lipophilicity is high and menstrual blood that has reached the embossed section is repelled into the excretory opening contact region.
[Blood Slipping Agent]

For the absorbent article of the present disclosure, the blood slipping agent has a kinematic viscosity of about 0.01 to about 80 mm$^2$/s at 40° C., a water holding percentage of about 0.05 to about 4.0 mass %, and a weight-average molecular weight of less than about 1000.

The blood slipping agent has, at 40° C., a kinematic viscosity of about 0 to about 80 mm$^2$/s, preferably a kinematic viscosity of about 1 to about 70 mm$^2$/s, more preferably a kinematic viscosity of about 3 to about 60 mm$^2$/s, even more preferably a kinematic viscosity of about 5 to about 50 mm$^2$/s, and yet more preferably a kinematic viscosity of about 7 to about 45 mm$^2$/s.

The kinematic viscosity tends to be higher with a) a larger molecular weight of the blood slipping agent, b) a higher percentage of polar bonds, such as carbonyl bonds (—CO—), ester bonds (—COO—), carbonate bonds (—OCOO—) and ether bonds (—O—), in groups, such as carbonyl groups (—CO—), oxy groups (—O—), carboxyl groups (—COOH), hydroxyl groups (—OH) and the like, and c) a larger IOB, explained below.

In order to have a kinematic viscosity of about 0 to about 80 mm$^2$/s at 40° C., the melting point of the blood slipping agent is preferably 45° C. or less. This is because the kinematic viscosity will tend to be higher if the blood slipping agent contains crystals at 40° C.

As used herein, the "kinematic viscosity at 40° C." may be referred to simply as "kinematic viscosity".

A kinematic viscosity exceeding about 80 mm$^2$/s will tend to result in high viscosity of the blood slipping agent, such that it will not as easily migrate into the absorbent body together with menstrual blood that has reached the skin contact surface of the top sheet.

The kinematic viscosity is measured according to JIS K 2283:2000, "5. Kinematic Viscosity Test Method", using a Cannon-Fenske reverse-flow viscometer, at a testing temperature of 40° C.

The blood slipping agent has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

As used herein, "water holding percentage" means the percentage of water that is held by a substance, and it is measured in the following manner.

(1) A test tube, a rubber stopper, the substance to be measured and deionized water are allowed to stand for a day and a night in a thermostatic chamber at 40° C.

(2) Into the 20 mL test tube in the thermostatic chamber there are charged 5.0 g of the substance to be measured and 5.0 g of deionized water.

(3) The mouth of the test tube is sealed with the rubber stopper in the thermostatic chamber, and it is rotated once and allowed to stand for 5 minutes.

(4) A 3.0 g portion of the layer of the substance to be measured (usually the upper layer) is sampled into a glass dish with a diameter of 90 mm (weight: $W_0$), in the thermostatic chamber.

(5) The dish is heated at 105° C. for 3 hours in an oven to evaporate off the moisture, and the weight of each dish is measured (weight: $W_1$).

(6) The water holding percentage is calculated by the following formula.

$$\text{Water holding percentage (\%)} = 100 \times (W_0 - W_1)/3.0$$

The measurement is conducted three times, and the average value is recorded.

A low water holding percentage value will tend to lower the affinity between the blood slipping agent and menstrual blood, thus impeding its migration together with menstrual blood that has reached the skin contact surface of the top sheet. If the water holding percentage value increases, on the other hand, the affinity between menstrual blood and the blood modifying agent will become very high, similar to a surfactant, and absorbed menstrual blood will tend to remain on the skin contact surface of the top sheet, resulting in more red coloration of the skin contact surface of the top sheet.

When the water holding percentage value increases, affinity with menstrual blood also drastically increases, and menstrual blood that has reached the embossed section will be less easily repelled into the excretory opening contact region.

The water holding percentage value tends to be greater with a) a smaller molecular weight of the blood slipping agent, and b) a higher percentage of polar bonds, such as carbonyl bonds (—CO—), ester bonds (—COO—), carbonate bonds (—OCOO—) and ether bonds (—O—), in groups, such as carbonyl groups (—CO—), oxy groups (—O—), carboxyl groups (—COOH), hydroxyl groups (—OH) and the like. This is because the blood slipping agent has greater hydrophilicity. The water holding percentage will tend to have a larger value with a greater IOB, i.e. with a higher inorganic value or with a lower organic value. This is because the blood slipping agent will have greater hydrophilicity.

The blood slipping agent has a weight-average molecular weight of less than about 1,000, and preferably a weight-average molecular weight of less than about 900. This is because, if the weight-average molecular weight is about 1,000 or higher, tack may result in the blood slipping agent itself, tending to create a feeling of unpleasantness for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor of the blood slipping agent during wear.

In addition, as used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 µL
Detection: RI (differential refractometer)

The weight-average molecular weights listed in the examples of the present specification were measured under the conditions described below.

The blood slipping agent can have an IOB of about 0.00 to about 0.60.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

When the IOB value increases, affinity with menstrual blood also drastically increases, and menstrual blood that has reached the embossed section will be less easily repelled into the excretory opening contact region.

The blood slipping agent preferably has a melting point of about 45° C. or less, and more preferably it has a melting point of about 40° C. or less. If the blood slipping agent has a melting point of about 45° C. or less, the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood slipping agent has a melting point of about 45° C. or less, it may be either liquid or solid at room temperature (25° C.), or in other words, the melting point may be either about 25° C. or higher or below about 25° C., and for example, it may have a melting point of about −5° C. or about −20° C.

The reason for a melting point of about 45° C. or less for the blood slipping agent will be explained below.

The blood slipping agent does not have a lower limit for the melting point thereof, but the vapor pressure is preferably low. The vapor pressure of the blood slipping agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere).

Considering that the absorbent article of the present disclosure is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure of the blood slipping agent is high, gasification may occur during storage and the amount may be reduced, often creating problems, such as odor during wear.

The melting point of the blood slipping agent may be selected depending on the weather or duration of wear. For example, in regions with a mean atmospheric temperature of about 10° C. or less, using a blood slipping agent with a melting point of about 10° C. or less helps the blood slipping agent function after excretion of menstrual blood, even if it has been cooled by the ambient temperature.

Also, when the absorbent article is to be used for a prolonged period of time, the melting point of the blood slipping agent is preferably at the high end of the range of about 45° C. or less. This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, a top sheet coated with a surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, does not have excessively high affinity with menstrual blood and therefore does not cause residue of menstrual blood on the top sheet and allows rapid migration into the absorbent body.

Preferably, the blood slipping agent is selected from the group consisting of following items (i)-(iii), and any combination thereof:

(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

More preferably, the blood slipping agent is selected from the group consisting of following items (i')-(iii'), and any combination thereof:

(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent has more preferably about 1.8 or less carbonyl bonds (—CO—), about 2 or less ester bonds (—COO—), about 1.5 or less carbonate bonds (—OCOO—), about 6 or less ether bonds (—O—), about 0.8 or less carboxyl groups (—COOH) and/or about 1.2 or less hydroxyl groups (—OH), per 10 carbon atoms in the hydrocarbon moiety.

Even more preferably, the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

The blood slipping agent in accordance with (A) to (F) will now be described in detail.

[(A) Ester of (A1) a Compound having a Chain Hydrocarbon Moiety and 2-4 Hydroxyl Groups Substituting for Hydrogens on the Chain Hydrocarbon Moiety, and (A2) a Compound having a Chain Hydrocarbon Moiety and 1 Carboxyl Group Substituting for a Hydrogen on the Chain Hydrocarbon Moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the kinematic viscosity, water holding percentage and weight-average molecular weight are within the aforementioned ranges.

Examples of (A1) a compound having a chain hydrocarbon moiety and 2-4 hydroxyl groups substituting for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituting for a hydrogen on the chain hydrocarbon moiety include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

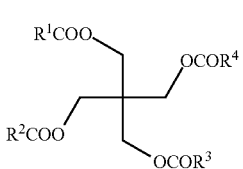

triesters of pentaerythritol and fatty acids, represented by the following formula (2):

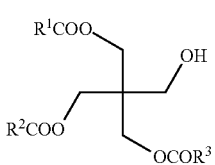

diesters of pentaerythritol and fatty acids, represented by the following formula (3):

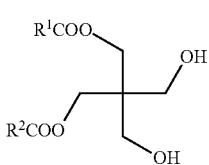

and monoesters of pentaerythritol and fatty acids, represented by the following formula (4).

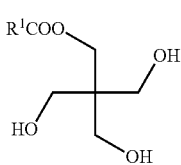

In the formulas, $R^1$-$R^4$ each represent a chain hydrocarbon.

The fatty acids consisting of the esters of pentaerythritol and fatty acids ($R^1COOH$, $R^2COOH$, $R^3COOH$, and $R^4COOH$) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and isomers thereof, such as 2-methylpropanoic acid ($C_4$), pentanoic acid ($C_5$) and isomers thereof, such as 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers thereof which are not described above.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, from the viewpoint of lowering the water holding percentage, the ester of pentaerythritol and a fatty acid is preferably a diester, triester or tetraester, more preferably a triester or tetraester, and even more preferably a tetraester.

From the viewpoint of the IOB being from about 0.00 to about 0.60, in a tetraester of pentaerythritol and a fatty acid, the total number of carbons of the fatty acid composing the tetraester of the pentaerythritol and fatty acid, i.e. the total number of carbons of the $R^1C$, $R^2C$, $R^3C$ and $R^4C$ portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid (C8), such as 2-ethylhexanoic acid ($C_8$), nonanoic acid ($C_9$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

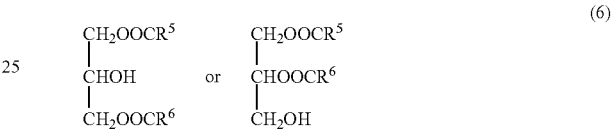

and monoesters of glycerin and fatty acids, represented by the following formula (7):

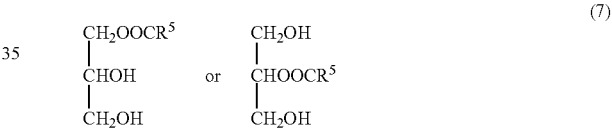

wherein $R^5$-$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, from the viewpoint of lowering the water holding percentage and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid (C12), tetradecanoic acid ($C_{14}$), hexadecanoic acid ($C_{16}$) and octadecanoic acid ($C_{18}$).

In order to obtain a melting point of about 45° C. or less, preferred triesters of glycerin and fatty acids are those with about 40 or less as the total number of carbons of the fatty acid consisting of the triester of glycerin and the fatty acid, i.e., the total number of carbons of the $R^5C$, $R^6C$ and $R^7C$ sections in formula (5).

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

(8)

wherein k represents an integer of 2-6, and $R^8$ and $R^9$ each represent a chain hydrocarbon, and monoesters of $C_2$-$C_6$ glycols and fatty acids, represented by the following formula (9):

(9)

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^9C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound having a Chain Hydrocarbon Moiety and 2-4 Hydroxyl Groups Substituting for Hydrogens on the Chain Hydrocarbon Moiety and (B2) a Compound having a Chain Hydrocarbon Moiety and 1 Hydroxyl Group Substituting for a Hydrogen on the Chain Hydrocarbon Moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety (hereunder also referred to as "compound (B)"), it is not necessary for all of the hydroxyl groups to be etherified so long as the kinematic viscosity, water holding percentage and weight-average molecular weight are within the aforementioned ranges.

Examples of (B1) a compound having a chain hydrocarbon moiety and 2-4 hydroxyl groups substituting for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituting for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and isomers thereof, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol (C17), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C═C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

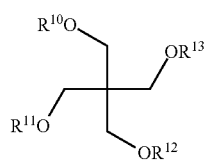

(10)

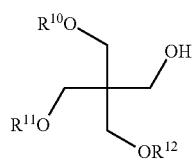

(11)

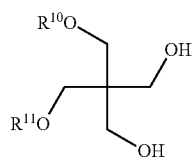

(12)

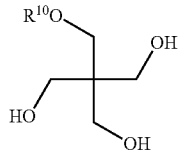

(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

$$\begin{array}{l} CH_2OR^{14} \\ | \\ CHOR^{15} \\ | \\ CH_2OR^{16} \end{array} \quad (14)$$

$$\begin{array}{l} CH_2OR^{14} \\ | \\ CHOH \\ | \\ CH_2OR^{15} \end{array} \quad \text{or} \quad \begin{array}{l} CH_2OR^{14} \\ | \\ CHOR^{15} \\ | \\ CH_2OH \end{array} \quad (15)$$

$$\begin{array}{l} CH_2OR^{14} \\ | \\ CHOH \\ | \\ CH_2OH \end{array} \quad \text{or} \quad \begin{array}{l} CH_2OH \\ | \\ CHOR^{14} \\ | \\ CH_2OH \end{array} \quad (16)$$

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R^{15}$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R^{17}$ portion is preferably about 8 or greater (the IOB is 0.60 when the number of carbon atoms is 8).

Compound (B) may be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting for Hydrogens on the Chain Hydrocarbon Moiety and (C2) a Compound having a Chain Hydrocarbon Moiety and 1 Hydroxyl Group Substituting for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the kinematic viscosity, water holding percentage and weight-average molecular weight are within the aforementioned ranges.

Examples of (C1) a carboxylic acid, hydroxy acid, alkoxy acid or oxoacid comprising a chain hydrocarbon moiety and 2-4 carboxyl groups substituting for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituting for a hydrogen on the chain hydrocarbon moiety includes those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, diisostearyl malate, tributyl citrate and tributyl O-acetylcitrate, of which commercially available products exist.

[(D) Compound having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \qquad (19)$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[($d_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of a fatty acid and an aliphatic monohydric alcohol include compounds having the following formula (21):

$$R^{23}COOR^{24} \qquad (21)$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "($a_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

The dialkyl carbonate may be a commercially available product, or it may be synthesized by reaction between phosgene and an alcohol, reaction between formic chloride and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, and ($d_4$) a dialkyl carbonate.

If the total number of carbon atoms is about 8 in a ($d_2$) dialkyl ketone, the melting point will be approximately −50° C. and the vapor pressure will be about 230 Pa at 20° C., in the case of 5-nonanone, for example.

[(E) Polyoxy $C_3$-$C_6$ Alkylene Glycol, or Alkyl Ester or Alkyl Ether Thereof]

The (E) polyoxy $C_3$-$C_6$ alkylene glycol, or alkyl ester or alkyl ether thereof (hereunder also referred to as "compound (E)") may be ($e_1$) a polyoxy $C_3$-$C_6$ alkylene glycol, ($e_2$) an ester of a polyoxy $C_3$-$C_6$ alkylene glycol and at least one fatty acid, or ($e_3$) an ether of a polyoxy $C_3$-$C_6$ alkylene glycol and at least one aliphatic monohydric alcohol. These will now be explained.

[($e_1$) Polyoxy $C_3$-$C_6$ Alkylene Glycol]

Polyoxy $C_3$-$C_6$ alkylene glycols refer to i) one or more homopolymers having a unit selected from the group consisting of oxy $C_3$-$C_6$ alkylene units, such as oxypropylene unit, oxybutylene unit, oxypentylene unit and oxyhexylene unit and having hydroxyl groups at both ends, ii) one or more block copolymers having 2 or more units selected from oxy $C_3$-$C_6$ alkylene units described above and oxyhexylene unit and having hydroxyl groups at both ends, or iii) random copolymers having 2 or more units selected from oxy $C_3$-$C_6$ alkylene units described above and having hydroxyl groups at both ends.

The polyoxy $C_3$-$C_6$ alkylene glycol can be represented by the following formula (23):

$$HO-(C_mH_{2m}O)_n-H \qquad (23)$$

wherein m represents an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol should be included in the ($e_1$) polyoxy $C_3$-$C_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n≥ about 7 (when n=7, the IOB is 0.57).

Examples of commercial products of poly $C_3$-$C_6$ alkylene glycols include UNIOL™ PB-500 and PB-700 (all products of NOF Corp.).

[($e_2$) Ester of a Polyoxy $C_3$-$C_6$ Alkylene Glycol and at Least One Fatty Acid]

Examples of an ester of a polyoxy $C_3$-$C_6$ alkylene glycol and at least one fatty acids include the polyoxy $C_3$-$C_6$ alkylene glycols mentioned for "($e_1$) Polyoxy $C_3$-$C_6$ alkylene glycol" in which one or both OH ends have been esterified with fatty acids, i.e. monoesters and diesters.

Examples of fatty acids to be esterified in the ester of a polyoxy $C_3$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

[(e₃) Ether of a Polyoxy $C_3$-$C_6$ Alkylene Glycol and at Least One Aliphatic Monohydric Alcohol]

Examples of an ether of a polyoxy $C_3$-$C_6$ alkylene glycols and at least one aliphatic monohydric alcohol include the polyoxy $C_3$-$C_6$ alkylene glycols mentioned for "(e₁) Polyoxy $C_3$-$C_6$ alkylene glycol" wherein one or both OH ends have been etherified by an aliphatic monohydric alcohol, i.e. monoethers and diethers.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include (f₁) chain alkanes, such as straight-chain alkanes and branched chain alkanes. Straight-chain alkanes with melting points of about 45° C. or less have up to about 22 carbon atoms, and at a vapor pressure of 1 atmosphere and about 0.01 Pa or less at 25° C., the number of carbon atoms is 13 or greater. Branched chain alkanes tend to have lower melting points than chain alkanes, given the same number of carbon atoms. Branched chain alkanes may therefore include those with 22 and more carbon atoms, even with melting points of below about 45° C.

Examples of commercially available hydrocarbon products include PARLEAM 6 (NOF Corp.).

The fibers composing such a woven fabric or nonwoven fabric as the liquid-permeable top sheet may be natural fibers or chemical fibers, with examples of natural fibers including cellulose, such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

The nonwoven fabric may also be a nonwoven fabric with a ridge-furrow structure comprising a plurality of ridges and a plurality of furrows, produced according to the method described in Japanese Unexamined Patent Publication No. 2008-2034.

Alternatively, the nonwoven fabric may be a nonwoven fabric with a ridge-furrow structure having a plurality of ridges and a plurality of furrows, produced according to the method described in Japanese Unexamined Patent Publication No. 2011-226010 or Japanese Unexamined Patent Publication No. 2011-226011. A nonwoven fabric with such a ridge-furrow structure can be formed by passing the nonwoven fabric to be treated through the gap between a pair of gear rolls with rotational axis lines that are perpendicular to the machine direction, and rotating while a plurality of teeth situated on the peripheral surfaces of each of the gear rolls are mutually engaged, and subjecting it to fluid treatment.

It is possible to form a top sheet with a plurality of ridges and a plurality of furrows extending in the lengthwise direction of the absorbent article, from a nonwoven fabric with such a ridge-furrow structure.

Liquid-impermeable back sheets include films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 g/m², for example, is preferred.

According to one embodiment of the absorbent article of the present disclosure, the absorbent article may comprise a second sheet between the liquid-permeable top sheet and the absorbent body. The second sheet may be any of the same examples as for the liquid-permeable top sheet.

The first example of the absorbent body is one having an absorbent core covered with a core wrap.

Examples of components for the absorbent core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super absorbent polymer, such as granules of a sodium acrylate copolymer or the like.

The core wrap is not particularly restricted so long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions so long as it is one that can be used in an absorbent article, such as a sanitary napkin.

The embossed section, and the optional additional embossed section, may be formed by a method known in the art, and for example, the embossed sections can be formed by using a pair of upper and lower embossing rolls, having a pattern formed on one of the rolls, for embossing of the top sheet and absorbent body (or the top sheet, second sheet and absorbent body) at a temperature below the melting point of the fibers and at a pressure of about 100 to about 1000 N/cm.

According to an embodiment of the absorbent article of the present disclosure, the top sheet within the excretory opening contact region contains a blood slipping agent on the surface on the skin side, i.e. on the skin contact surface. According to another embodiment of the absorbent article of the present disclosure, the top sheet within the excretory opening contact region contains a blood slipping agent on the skin contact surface and in the interior between the skin contact surface and the clothing side surface. According to yet another embodiment of the absorbent article of the present disclosure, the top sheet within the excretory opening contact region contains a blood slipping agent over the entire thickness direction, i.e. on the skin contact surface, in the interior between the skin contact surface and the clothing side surface, and on the clothing side surface. If the blood slipping agent is present in the top sheet interior and/or on the clothing side surface, menstrual blood present on the skin contact surface will be able to rapidly migrate into the absorbent body.

According to another embodiment of the absorbent article of the present disclosure, embossed section and the optional additional embossed section contain a blood slipping agent on the skin contact surface and in the interior between the skin contact surface and the clothing side surface. According to yet another embodiment of the absorbent article of the present disclosure, the embossed section and the optional additional embossed section contain a blood slipping agent over the entire thickness direction, i.e. on the skin contact surface, in the interior between the skin contact surface and the clothing side surface, and on the clothing side surface. If a blood slipping agent is present inside the embossed section and optionally the additional embossed section and/or on the clothing side surface, menstrual blood that has reached that area will be easily repelled into the excretory opening contact region.

The blood slipping agent preferably does not obstruct the voids between the fibers of the nonwoven fabric or woven fabric composing the top sheet, and for example, the blood slipping agent may be attached as droplets or particulates on the surface of the nonwoven fabric or woven fabric fibers, or covering the surfaces of the fibers.

In order for the blood slipping agent to migrate together with the absorbed menstrual blood, and to repel menstrual blood, it preferably has a large surface area, and a blood slipping agent present as droplets or particulates preferably has a small droplet/particle size.

Preferably, the fibers composing the nonwoven fabric and woven fabric as the liquid-permeable top sheet are either coated on their surfaces with a hydrophilic agent, or the fiber starting material is mixed with a hydrophilic agent for hydrophilicizing treatment of the surfaces. This is because, if the fibers are hydrophilic, there will be lipophilic regions due to the blood slipping agent and hydrophilic regions due to the hydrophilic agent sparsely dispersed on the top sheet, which will facilitate migration of menstrual blood.

In an embodiment in which the domed section comprises a blood slipping agent, there are no particular restrictions on the method of coating the blood slipping agent, and coating may be accomplished with heating as necessary, using a non-contact coater, such as for example, a spiral coater, curtain coater, spray coater or dip coater, or a contact coater or the like. A non-contact coater is preferred from the viewpoint of uniformly dispersing the droplet or particulate blood slipping agent throughout, and from the viewpoint of not causing damage in the top sheet. The blood slipping agent may be coated directly, if it is a liquid at room temperature, or it may be heated to lower the viscosity, and when it is a solid at room temperature, it may be heated to liquefaction and coated through a control seam hot melt adhesive (HMA) gun. By increasing the air pressure of the control seam HMA gun, it is possible to coat the blood slipping agent as fine particulates.

There are also no particular restrictions on the method of forming an absorbent article having a greater amount of blood slipping agent in the embossed section and the optional additional embossed section than the amount of blood slipping agent in the top sheet within the excretory opening contact region, and for example, it may be one in which (I) the embossed section and the optional additional embossed section are liberally coated with a reduced amount of blood slipping agent discharged from a control seam HMA gun, or (II) the embossed section and optional additional embossed section are liberally coated with a curtain coater. In addition, (III) heating may be carried out to lower the viscosity of the blood slipping agent, and the blood slipping agent coated onto the heated top sheet, the heated state being maintained thereafter, so that a fixed amount of the coated blood slipping agent migrates into the embossed section and the optional additional embossed section.

In an embodiment in which the domed section comprises a blood slipping agent, the blood slipping agent may be coated during production of the material for the top sheet and/or second sheet, such as the nonwoven fabric, or it may be coated in the manufacturing line for production of the absorbent article. In an embodiment in which the domed section comprises a blood slipping agent, from the viewpoint of minimizing equipment investment, the blood slipping agent is preferably coated in the manufacturing line for the absorbent article, and in order to prevent shedding of the blood slipping agent which may contaminate the line, the blood slipping agent is preferably coated during a step downstream from the manufacturing line, and specifically, immediately before encapsulation of the product in an individual package.

The blood slipping agent also has an effect as a lubricant. Thus, the blood slipping agent reduces friction between the fibers, and can improve flexibility across the entire nonwoven fabric or woven fabric.

According to a preferred embodiment of the absorbent article of the present disclosure, the absorbent article is one that is intended for absorption of menstrual blood, such as a sanitary napkin or panty liner.

An absorbent article of the present disclosure does not require components, such as emollients and immobilizing agents, unlike in an absorbent article containing a known skin care composition, lotion composition or the like, and the blood slipping agent alone may be applied to the top sheet.

EXAMPLES

The present disclosure will now be explained in fuller detail by examples, with the understanding that it is not meant to be limited to the examples.

Example 1

[Evaluation of Rewetting Rate and Absorbent Body Migration Rate]

A commercially available sanitary napkin was prepared, as shown in FIG. 1. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood slipping agents used for testing are listed below.
[($a_1$) Ester of a Chain Hydrocarbon Tetraols and at Least One Fatty Acid]

UNISTAR H-408BRS, product of NOF Corp.

Pentaerythritol tetra(2-ethylhexanoate), weight-average molecular weight: approximately 640

UNISTAR H-2408BRS-22, product of NOF Corp.

Mixture of pentaerythritol tetra(2-ethylhexanoate) and neopentylglycol di(2-ethylhexanoate) (58:42 as weight ratio), weight-average molecular weight: approximately 520
[($a_2$) Ester of a Chain Hydrocarbon Triols and at Least One Fatty Acid]

Cetiol SB45DEO, Cognis Japan

Glycerin and fatty acid triester, with oleic acid or stearylic acid as the fatty acid.

SOY42, product of NOF Corp.

Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L oil fatty acid glyceride, product of NOF Corp.

Glycerin and fatty acid triester with $C_8$ fatty acid:$C_{10}$ fatty acid:$C_{12}$ fatty acid at a mass ratio of about 37:7:56, weight-average molecular weight: approximately 570
    Tri-CL oil fatty acid glyceride, product of NOF Corp.
Glycerin and fatty acid triester with $C_8$ fatty acid:$C_{12}$ fatty acid at a mass ratio of about 44:56, weight-average molecular weight: approximately 570
    PANACET 810s, product of NOF Corp.
Glycerin and fatty acid triester with $C_8$ fatty acid:$C_{10}$ fatty acid at a mass ratio of about 85:15, weight-average molecular weight: approximately 480
    PANACET 800, product of NOF Corp.
Glycerin and fatty acid triester with octanoic acid (C8) as the entire fatty acid portion, weight-average molecular weight: approximately 470
    PANACET 800B, product of NOF Corp.
Glycerin and fatty acid triester with 2-ethylhexanoic acid ($C_8$) as the entire fatty acid portion, weight-average molecular weight: approximately 470
    NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880
    Tri-Coconut Fatty Acid Glyceride, Product of NOF Corp.
Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670
    Caprylic acid diglyceride, product of NOF Corp.
Glycerin and fatty acid diester with octanoic acid as the fatty acid, weight-average molecular weight: approximately 340

[($a_3$) Ester of a Chain Hydrocarbon Diol and at Least One Fatty Acid]
    UNISTAR H-208BRS, product of NOF Corp.
    Neopentyl glycol di(2-ethylhexanoate), weight-average molecular weight: approximately 360
    COMPOL BL, product of NOF Corp.
    Dodecanoic acid ($C_{12}$) monoester of butylene glycol, weight-average molecular weight: approximately 270
    COMPOL BS, product of NOF Corp.
    Octadecanoic acid ($C_{18}$) monoester of butylene glycol, weight-average molecular weight: approximately 350

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]
    Tributyl O-acetylcitrate, product of Tokyo Kasei Kogyo Co., Ltd.
    Weight-average molecular weight: approximately 400
    Tributyl citrate, product of Tokyo Kasei Kogyo Co., Ltd.
    Weight-average molecular weight: approximately 360

[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]
    Dioctyl adipate, product of Wako Pure Chemical Industries, Ltd.
    Weight-average molecular weight: approximately 380

[($d_3$) Ester of a Fatty Acid and an Aliphatic Monohydric Alcohol]
    ELECTOL WE20, product of NOF Corp.
    Ester of dodecanoic acid ($C_{12}$) and dodecyl alcohol ($C_{12}$), weight-average molecular weight: approximately 360
    ELECTOL WE40, product of NOF Corp.
    Ester of tetradecanoic acid ($C_{14}$) and dodecyl alcohol ($C_{12}$), weight-average molecular weight: approximately 390

[($e_1$) Polyoxy $C_3$-$C_6$ Alkylene Glycol]
    UNIOL PB500, product of NOF Corp.
    Polybutylene glycol, weight-average molecular weight: approximately 500
    UNIOL PB700, product of NOF Corp.
    Polyoxybutylene polyoxypropylene glycol, weight-average molecular weight: approximately 700

[($f_1$) Chain Alkane]
    PARLEAM 6, product of NOF Corp.
    Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]
    NA50, Product of NOF Corp.
    Glycerin and fatty acid triester obtained by addition of hydrogen to NA36 for reduced proportion of double bonds from unsaturated fatty acid starting material, weight-average molecular weight: approximately 880
        (Caprylic acid/capric acid) monoglyceride, product of NOF Corp.
    Glycerin and fatty acid monoester, with octanoic acid ($C_8$) and decanoic acid ($C_{10}$) at a mass ratio of about 85:15, weight-average molecular weight: approximately 220
        Monomuls 90-L2 lauric acid monoglyceride, product of Cognis Japan
        Isopropyl citrate, product of Tokyo Kasei Kogyo Co., Ltd.
        Weight-average molecular weight: approximately 230
        Diisostearyl Malate
        Weight-average molecular weight: approximately 640
    UNIOL PB1000R, product of NOF Corp.
    Polybutylene glycol, weight-average molecular weight: approximately 1,000
    UNIOL D-250, product of NOF Corp.
    Polypropylene glycol, weight-average molecular weight: approximately 250
    UNIOL D-400, product of NOF Corp.
    Polypropylene glycol, weight-average molecular weight: approximately 400
    UNIOL D-700, product of NOF Corp.
    Polypropylene glycol, weight-average molecular weight: approximately 700
    UNIOL D-1000, product of NOF Corp.
    Polypropylene glycol, weight-average molecular weight: approximately 1,000
    UNIOL D-1200, product of NOF Corp.
    Polypropylene glycol, weight-average molecular weight: approximately 1,160
    UNIOL D-2000, product of NOF Corp.
    Polypropylene glycol, weight-average molecular weight: approximately 2,030
    UNIOL D-3000, product of NOF Corp.
    Polypropylene glycol, weight-average molecular weight: approximately 3,000
    UNIOL D-4000, product of NOF Corp.
    Polypropylene glycol, weight-average molecular weight: approximately 4,000
    PEG1500, product of NOF Corp.
    Polyethylene glycol, weight-average molecular weight: approximately 1,500-1,600
    WILBRITE cp9, product of NOF Corp.
    Polybutylene glycol compound with OH groups at both ends esterified by hexadecanoic acid ($C_{16}$), weight-average molecular weight: approximately 1,150
    UNILUBE MS-70K, product of NOF Corp.

Stearyl ether of polypropylene glycol, approximately 15 repeating units, weight-average molecular weight: approximately 1,140

NONION S-6, product of NOF Corp.

Polyoxyethylene monostearate, approximately 7 repeating units, weight-average molecular weight: approximately 880

UNILUBE 5TP-300KB

Polyoxyethylene polyoxypropylene pentaerythritol ether, produced by addition of 5 mol of ethylene oxide and 65 mol of propylene oxide to 1 mol of pentaerythritol, weight-average molecular weight: 4,130

WILBRITE s753, product of NOF Corp.

Polyoxyethylene polyoxypropylene polyoxybutylene glycerin, weight-average molecular weight: approximately 960

UNIOL TG-330, product of NOF Corp.

Glyceryl ether of polypropylene glycol, approximately 6 repeating units, weight-average molecular weight: approximately 330

UNIOL TG-1000, product of NOF Corp.

Glyceryl ether of polypropylene glycol, approximately 16 repeating units, weight-average molecular weight: approximately 1,000

UNIOL TG-3000, product of NOF Corp.

Glyceryl ether of polypropylene glycol, approximately 16 repeating units, weight-average molecular weight: approximately 3,000

UNIOL TG-4000, product of NOF Corp.

Glyceryl ether of polypropylene glycol, approximately 16 repeating units, weight-average molecular weight: approximately 4,000

UNILUBE DGP-700, product of NOF Corp.

Diglyceryl ether of polypropylene glycol, approximately 9 repeating units, weight-average molecular weight: approximately 700

UNIOX HC60, product of NOF Corp.

Polyoxyethylene hydrogenated castor oil, weight-average molecular weight: approximately 3,570

Vaseline, product of Cognis Japan

Petroleum-derived hydrocarbon, semi-solid

The kinematic viscosities, water holding percentages, weight-average molecular weights, IOBs and melting points of the samples are shown in Table 2.

For the melting point, "<45" indicates a melting point of below 45° C.

Almost the entire skin contact surface of the top sheet of the sanitary napkin was coated with the aforementioned blood slipping agent. Each blood slipping agent was used directly, when it was liquid at room temperature, or when the blood slipping agent was solid at room temperature it was heated to its melting point of +20° C., and then a control seam HMA gun was used for atomization of each blood slipping agent and coating onto the skin contact surface of the top sheet to a basis weight of about 5 g/m².

Figure 3:
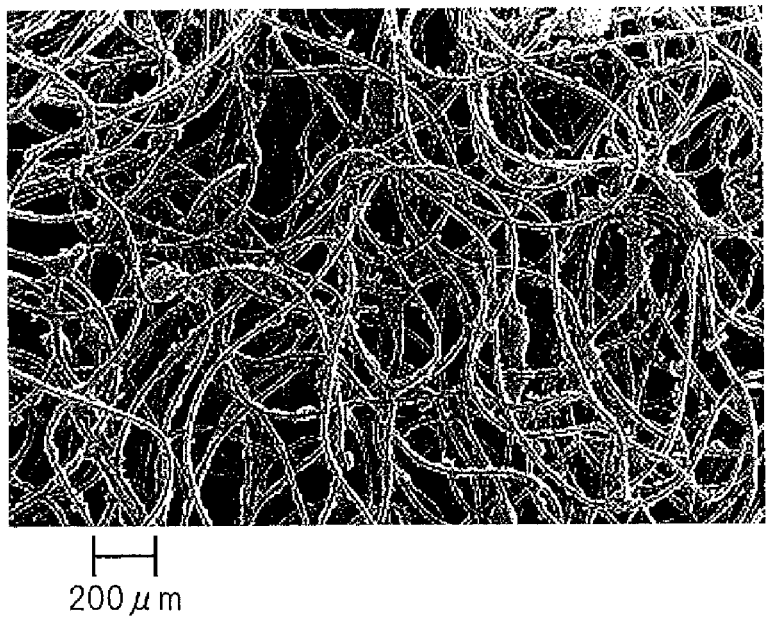
FIG. 3 is an electron micrograph of the skin contact surface of a top sheet in a sanitary napkin wherein the top sheet comprises tri-C2L oil fatty acid glycerides.

FIG. 3 is an electron micrograph of the skin contact surface of a top sheet in a sanitary napkin (No. 1-5) wherein the top sheet comprises tri-C2L oil fatty acid glycerides. As clearly seen in FIG. 3, the tri-C2L oil fatty acid glycerides are present on the fiber surfaces as fine particulates.

[Test Methods]

An acrylic board with an opened hole (200 mm×100 mm, 125 g, with a 40 mm×10 mm hole opened at the center) was placed on a top sheet comprising each blood slipping agent, and 3 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3 g of horse EDTA blood at 37±1° C. was again added dropwise through the acrylic board hole with a pipette (twice).

After the second dropping of blood, the acrylic board was immediately removed and 10 sheets of filter paper (Qualitative filter paper No. 2, product of Advantech Toyo, Inc., 50 mm×35 mm) were placed on the location where the blood had been dropped, and then a weight was placed thereover to a pressure of 30 g/cm². After 1 minute, the filter paper was removed and the "rewetting rate" was calculated by the following formula.

Rewetting rate (%)=100×(filter paper mass after test− initial filter paper mass)/6

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

The whiteness of the skin contact surface of the top sheet (TS) after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The tack on the skin contact surface of the top sheet was also measured at 35° C., and evaluated on the following scale.

G: No tack
F: Slight tack
P: Tack

The results are summarized in Table 2 below.

TABLE 2

| No. | Blood lubricity imparter | Kinematic viscosity (mm²/s, 40° C.) | Water holding percentage (mass %) | Weight-average mol. wt. | IOB | Melting pt. (° C.) | Rewetting rate (%) | Absorbent body migration rate (sec) | TS whiteness | Tack |
|---|---|---|---|---|---|---|---|---|---|---|
| 1-1 | H-408BRS | 45 | 0.7 | 640 | 0.13 | <−5 | 1.2 | 3 | VG | G |
| 1-2 | H-2408BRS-22 | 22 | 0.8 | 520 | 0.18 | <−5 | 2.0 | 3 | VG | G |
| 1-3 | Cetiol SB45DEO | | | | 0.16 | 44 | 7.0 | 6 | VG | |
| 1-4 | SOY42 | | | 880 | 0.16 | 43 | 5.8 | 8 | VG | G |
| 1-5 | Tri-C2L oil fatty acid glycerides | 20 | <1.0 | 570 | 0.27 | 37 | 0.3 | 3 | VG | G |
| 1-6 | Tri-CL oil fatty acid glycerides | 15 | <1.0 | 570 | 0.28 | 38 | 1.7 | 3 | VG | G |

TABLE 2-continued

| No. | Blood lubricity imparter | Kinematic viscosity (mm²/s, 40° C.) | Water holding percentage (mass %) | Weight-average mol. wt. | IOB | Melting pt. (° C.) | Rewetting rate (%) | Absorbent body migration rate (sec) | TS whiteness | Tack |
|---|---|---|---|---|---|---|---|---|---|---|
| 1-7 | PANACET 810s | 9 | 0.3 | 480 | 0.32 | −5 | 2.8 | 3 | VG | G |
| 1-8 | PANACET 800 | 15 | 0.5 | 470 | 0.33 | −5 | 0.3 | 3 | VG | G |
| 1-9 | PANACET 800B | 20 | <1.0 | 470 | 0.33 | −5 | 2.0 | 3 | VG | G |
| 1-10 | NA36 | 40 | <1.0 | 880 | 0.16 | 37 | 3.9 | 5 | VG | G |
| 1-11 | Tri-coconut oil fatty acid glycerides | 25 | <1.0 | 670 | 0.28 | 30 | 4.3 | 5 | VG | G |
| 1-12 | Caprylic acid diglyceride | 25 | 2.7 | 340 | 0.58 | <45 | 4.2 | 9 | G | G |
| 1-13 | UNISTAR H-208BRS | 8 | 0.7 | 360 | 0.24 | <−5 | 2.0 | 5 | VG | G |
| 1-14 | COMPOL BL | 10 | 1.6 | 270 | 0.50 | 2 | 2.0 | 5 | G | G |
| 1-15 | COMPOL BS | 35 | 0.3 | 350 | 0.36 | 37 | 7.9 | 9 | G | G |
| 1-16 | Tributyl O-acetylcitrate | 15 | 0.9 | 400 | 0.60 | <45 | 6.2 | 8 | VG | G |
| 1-17 | Tributyl citrate | 12 | 0.6 | 360 | 0.78 | <45 | 3.0 | 6 | G | G |
| 1-18 | Dioctyl adipate | 7 | 0.4 | 380 | 0.27 | <45 | 1.7 | 6 | VG | G |
| 1-19 | ELECTOL WE20 | 10 | 0.3 | 360 | 0.13 | 29 | 1.8 | 5 | VG | G |
| 1-20 | ELECTOL WE40 | 15 | 0.5 | 390 | 0.12 | 37 | 1.8 | 4 | VG | G |
| 1-21 | UNIOL PB500 | 40 | 3.6 | 500 | 0.44 | <45 | 4.5 | 4 | G | G |
| 1-22 | UNIOL PB700 | 50 | 2.3 | 700 | 0.49 | −5 | 2.8 | 5 | G | G |
| 1-23 | PARLEAM 6 | 5 | 0.06 | 330 | 0.00 | −5 | 6.0 | 8 | VG | G |
| 1-24 | NA50 | 80<< | —* | 880 | 0.18 | 52 | 15.5 | 60 | P | G |
| 1-25 | (Caprylic acid/Capric acid) monoglyceride | 70 | 4.0<< | 220 | 1.15 | <45 | 4.0 | 4 | P | G |
| 1-26 | 90-L2 Lauric acid monoglyceride | 80<< | 4.0<< | <1,000 | 0.87 | 58 | 6.2 | 7 | P | G |
| 1-27 | Isopropyl citrate | 120 | 4.0<< | 230 | 1.56 | <45 | 12.2 | 5 | G | F |
| 1-28 | Diisostearyl malate | 450 | 4.0<< | 640 | 0.28 | <45 | 5.5 | 8 | F | F |
| 1-29 | UNIOL PB1000R | 70 | 5.5 | 1000 | 0.40 | <45 | 4.0 | 4 | G | F |
| 1-30 | UNIOL D-250 | 20 | 4.0<< | 250 | | <45 | — | — | P | G |
| 1-31 | UNIOL D-400 | 30 | 4.0<< | 400 | 0.76 | <45 | 8.7 | 40 | P | G |
| 1-32 | UNIOL D-700 | 50 | 34.6 | 700 | 0.58 | <45 | 7.5 | — | F | G |
| 1-33 | UNIOL D-1000 | 70 | 26.7 | 1,000 | 0.51 | <45 | 6.8 | 15 | F | F |
| 1-34 | UNIOL D-1200 | 90 | 16.2 | 1,160 | 0.48 | <45 | 0.5 | 11 | F | F |
| 1-35 | UNIOL D-2000 | 160 | | 2,030 | | <45 | — | — | F | P |
| 1-36 | UNIOL D-3000 | | 0.6 | 3,000 | 0.39 | <45 | 1.7 | 10 | F | P |
| 1-37 | UNIOL D-4000 | 450 | 0.5 | 4,000 | 0.38 | <45 | 1.0 | 7 | G | P |
| 1-38 | PEG1500 | 120 | 4.0<< | 1,500-1,600 | 0.78 | 40 | 11.0 | 38 | P | P |
| 1-39 | WILBRITE CP9 | 120 | 0.6 | 1,150 | 0.21 | 35 | 1.4 | 3 | G | P |
| 1-40 | UNILUBE MS-70K | 50 | 2.8 | 1,140 | 0.30 | <−10 | 6.7 | 3 | G | F |
| 1-41 | NONION S-6 | 65 | 4.0<< | 880 | 0.44 | 37 | 8.4 | 7 | P | G |
| 1-42 | UNILUBE 5TP-300KB | 310 | 3.9 | 4,130 | 0.39 | <45 | 2.0 | 6 | G | P |
| 1-43 | WILBRITE s753 | 120 | 27.3 | 960 | 0.67 | −5 | 9.3 | 9 | F | F |
| 1-44 | UNIOL TG-330 | 30 | | 330 | 1.27 | <45 | — | — | — | G |
| 1-45 | UNIOL TG-1000 | 100 | 21.2 | 1,000 | 0.61 | <45 | 14.2 | 7 | G | G |
| 1-46 | UNIOL TG-3000 | 230 | 4.3 | 3,000 | 0.42 | <45 | 0.8 | 6 | G | P |
| 1-47 | UNIOL TG-4000 | 300 | 2.4 | 4,000 | 0.40 | <45 | 2.0 | 6 | G | P |
| 1-48 | UNILUBE DGP-700 | 200 | 4.0<< | 700 | 0.91 | <0 | 8.0 | 10 | F | F |
| 1-49 | UNIOX HC60 | 1150 | | 3,570 | 0.46 | 33 | 14.6 | 46 | P | P |
| 1-50 | Vaseline | 80<< | 0.0 | <1,000 | 0.00 | 55 | 9.7 | 10 | F | P |
| 1-51 | None | — | — | — | — | — | 22.7 | 60< | P | G |

*Viscosity too high for measurement.

In the absence of a blood slipping agent, the rewetting rate was 22.7% and the absorbent body migration rate was greater than 60 seconds, but the glycerin and fatty acid triesters all produced rewetting rates of 7.0% or less and absorbent body migration rates of no longer than 8 seconds, and therefore significantly improved the absorption performance.

Similarly, it was found that the absorption performance is greatly improved with a blood slipping agent having a kinematic viscosity of about 0.01 to 80 mm²/s at 40° C., a water holding percentage of about 0.01 to about 4.0 mass %, and a weight-average molecular weight of less than about 1000.

Next, several volunteer subjects were asked to wear sanitary napkins Nos. 1-1 to 1-51, and the obtained responses indicated that with the sanitary napkins comprising blood slipping agent Nos. 1-1 to 1-23, the top sheets had no sticky feel and the top sheets were smooth, even after absorption of menstrual blood.

Also, with sanitary napkins that comprised blood slipping agent Nos. 1-11, 13, 16, 18-20 and 23, the skin contact surfaces of the top sheets after absorption of menstrual blood had not been reddened by the blood and the unpleasantness was minimal.

The responses also indicated that with sanitary napkins comprising blood slipping agent Nos. 1-1 to 1-23, menstrual blood tended to diffuse through the embossed section and the additional embossed section with more difficulty on the top sheet. Example 1 is not an example where the amount of blood slipping agent in the embossed section or additional embossed section is greater than the amount of blood slipping agent in the top sheet within the excretory opening contact region, but it suggests that diffusion of menstrual blood on the top sheet can be further inhibited by increasing the amount of blood slipping agent in the embossed section and additional embossed section.

Example 2

[Surface Residue Rate of Menstrual Blood on Top Sheet with Ridge-furrow Structure]

The surface residue rate of menstrual blood on a top sheet with a ridge-furrow structure was evaluated.

There were prepared a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, the pitch of the ridge-furrow structure (ridge width+furrow width) was approximately 4 mm, and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m$^2$. With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 2-1.

Sanitary napkins No. 2-2 to No. 2-40 were produced, changing the blood slipping agent from UNISTAR H-408BRS to the ones listed in Table 3. Each blood slipping agent was used directly, when it was liquid at room temperature, or when the blood slipping agent was solid at room temperature it was heated to its melting point of +20° C., and then a control seam HMA gun was used for atomization of the blood slipping agent and coating onto the skin contact surface of the top sheet to a basis weight of about 5 g/m$^2$.

The blood slipping agent was coated onto essentially the entire skin contact surface of the top sheet, and on both the ridges and furrows.

[Test Methods]

After measuring the weight $W_2$ of the top sheet (the weight of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the weight $W_3$ (weight of top sheet after the test) was measured and the "surface residue rate (mass %)" was calculated by the following formula.

Surface residue rate (mass %)=100×($W_3$−$W_2$)/4.0

The results are summarized in Table 3 below.

TABLE 3

| No. | Blood slipping agent | Surface residue rate (mass %) |
|---|---|---|
| 2-1 | H-408BRS | 0.8 |
| 2-2 | H-2408BRS-22 | 0.8 |
| 2-3 | PANACET 810s | 0.8 |
| 2-4 | PANACET 800 | 1.8 |
| 2-5 | Caprylic acid diglyceride | 1.0 |
| 2-6 | UNISTAR H-208BRS | 0.5 |
| 2-7 | COMPOL BL | 1.3 |
| 2-8 | COMPOL BS | 2.5 |
| 2-9 | Tributyl O-acetylcitrate | 0.5 |
| 2-10 | Tributyl citrate | 1.8 |
| 2-11 | Dioctyl adipate | 1.5 |
| 2-12 | ELECTOL WE20 | 0.5 |
| 2-13 | ELECTOL WE40 | 2.3 |
| 2-14 | UNIOL PB500 | 2.5 |
| 2-15 | UNIOL PB700 | 1.3 |
| 2-16 | PARLEAM 6 | 2.0 |
| 2-17 | NA50 | 4.3 |
| 2-18 | (Caprylic acid/capric acid) monoglyceride | 5.0 |
| 2-19 | 90-L2 Lauric acid monoglyceride | 5.0 |
| 2-20 | Isopropyl citrate | 4.8 |
| 2-21 | Diisostearyl malate | 3.3 |
| 2-22 | UNIOL PB1000R | 2.5 |
| 2-23 | UNIOL D-250 | 3.8 |
| 2-24 | UNIOL D-400 | 4.8 |
| 2-25 | UNIOL D-700 | 4.8 |
| 2-26 | UNIOL D-1000 | 3.8 |
| 2-27 | UNIOL D-1200 | 3.0 |
| 2-28 | UNIOL D-3000 | 3.0 |
| 2-29 | UNIOL D-4000 | 2.5 |
| 2-30 | PEG1500 | 5.5 |
| 2-31 | WILBRITE CP9 | 6.8 |
| 2-32 | UNILUBE MS-70K | 1.5 |
| 2-33 | UNILUBE 5TP-300KB | 2.0 |
| 2-34 | WILBRITE s753 | 3.5 |
| 2-35 | UNIOL TG-1000 | 3.5 |
| 2-36 | UNIOL TG-3000 | 1.0 |
| 2-37 | UNIOL TG-4000 | 2.0 |
| 2-38 | UNILUBE DGP-700 | 3.5 |
| 2-39 | Vaseline | 4.0 |
| 2-40 | None | 7.5 |

With sanitary napkin No. 2-40, which had no blood slipping agent, the surface residue rate was 7.5 mass %, but with sanitary napkins No. 2-1 to No. 2-16 wherein the kinematic viscosity and water holding percentage were within the prescribed ranges, the surface residue rate was 2.5 mass % or lower.

With sanitary napkins No. 2-1 to No. 2-16, it was observed that the horse EDTA blood that was dropped onto the ridges of the top sheet slipped down from the ridges into the furrows, and was rapidly absorbed from the furrows into the absorbent body. However, with sanitary napkin No. 2-40 which had no blood slipping agent, the dropped horse EDTA blood did not slip down into the furrows but slowly dripped down into the furrows, most of it remaining on the ridges of the top sheet. Also, with the absorbent articles with high water holding percentage, as with No. 2-25, for example, the horse EDTA blood that was dropped onto the ridges of the top sheet did not slip down into the furrows but slowly dripped while partially remaining on the top sheet, and a portion thereof remained on the ridges.

The following experiment was also conducted in order to confirm the function of the blood slipping agent.

Example 3

[Viscosity of Blood Containing Blood Slipping Agent]

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and the blood slipping agent of the present disclosure has an effect of lowering the viscosity of blood, such as menstrual blood in the low viscosity range. Lowering the blood viscosity allows absorbed menstrual blood to more easily migrate rapidly from the top sheet to the absorbent body.

Example 4

[Photomicrograph of Blood Slipping Agent-containing Menstrual Blood]

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 4(a), and a photomicrograph of menstrual blood containing PANACET 810s is shown in FIG. 4(b).

Figure 4:
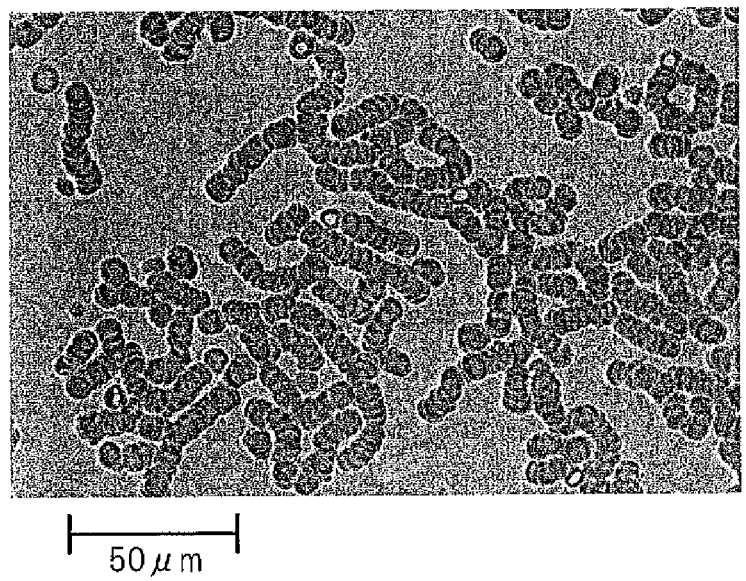
FIG. 4 is a pair of photomicrographs of menstrual blood containing and not containing a blood slipping agent.
Figure 4:
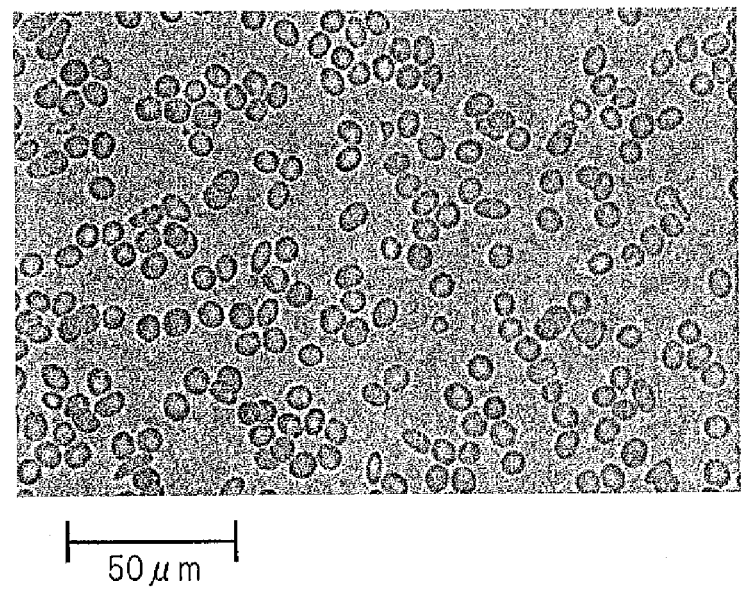

FIG. 4(a) shows that the erythrocytes formed aggregates, including a rouleaux structure, in the menstrual blood containing no blood slipping agent, while FIG. 4(b) shows that the erythrocytes were stably dispersed in the menstrual blood containing PANACET 810s. This suggests that the blood slipping agent has the function of stabilizing erythrocytes in menstrual blood.

Example 5

[Surface Tension of Blood Containing Blood Slipping Agent]

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

The measurement was accomplished automatically with a device, and the surface tension γ was determined by the following formula (see FIG. 5).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 4, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 4 below.

TABLE 4

| | Blood slipping agent | | Measuring | Surface |
| No. | Type | Amount (mass %) | temperature (° C.) | tension (mN/m) |
| --- | --- | --- | --- | --- |
| 4-1 | — | — | 35 | 62.1 |
| 4-2 | PANACET | 0.01 | 35 | 61.5 |
| 4-3 | 810s | 0.05 | 35 | 58.2 |
| 4-4 | | 0.10 | 35 | 51.2 |
| 4-5 | ELECTOL WE20 | 0.10 | 35 | 58.8 |
| 4-6 | PARLEAM 6 | 0.10 | 35 | 57.5 |
| 4-7 | — | — | 50 | 56.3 |
| 4-8 | WILBRITE cp9 | 0.10 | 50 | 49.1 |

Based on Table 4 it is seen that the blood slipping agent has an effect of lowering the surface tension of blood.

Lowering the surface tension of blood allows absorbed blood to rapidly migrate from the top sheet to the absorbent body, without being retained between the top sheet fibers.

The present disclosure relates to the following J1 to J15.

[J1]

An absorbent article comprising a liquid-permeable top sheet, formed from a nonwoven fabric or woven fabric, a liquid-impermeable back sheet, and an absorbent body between the top sheet and the back sheet, wherein the absorbent article has an excretory opening contact region that contacts with the excretory opening of the wearer, and an embossed section which is continuously or discontinuously disposed and which surrounds the excretory opening contact region, the embossed section is formed by embossing the layer comprising the top sheet and the absorbent body, the top sheet within the excretory opening contact region and the embossed section each comprise a blood slipping agent that has a kinematic viscosity of 0.01 to 80 mm$^2$/s at 40° C., a water holding percentage of 0.01 to 4.0 mass % and a weight-average molecular weight of less than 1000, and the basis weight of the blood slipping agent in the embossed section is greater than the basis weight of blood slipping agent in the top sheet within the excretory opening contact region.

[J2]

The absorbent article according to J1, wherein the blood slipping agent further has an IOB of 0.00-0.60.

[J3]

The absorbent article according to J1 or J2, wherein the embossed section is discontinuously disposed and surrounds the excretory opening contact region, and one or more additional embossed sections are further disposed on the outer sides of the embossed section.

[J4]

The absorbent article according to J3, wherein the one or more additional embossed sections are disposed on the outer sides of discontinuous portions of the embossed section.

[J5]

The absorbent article according to J3 or J4, wherein the one or more additional embossed sections comprise the blood slipping agent, and the basis weight of blood slipping agent in the additional embossed sections is greater than the basis weight of blood slipping agent in the top sheet within the excretory opening contact region.

[J6]

The absorbent article according to any one of J1 to J5, wherein the absorbent article comprises second embossed section disposed on the outer side of the excretory opening contact region in the lengthwise direction, and formed by embossing the layer comprising the top sheet and absorbent body.

[J7]

The absorbent article according to J6, wherein the second embossed section is disposed and curved so as to surround the edge of the excretory opening contact region in the lengthwise direction.

[J8]

The absorbent article according to any one of J1 to J7, wherein the absorbent article further comprises a second sheet between the top sheet and the absorbent body, and the embossed sections are formed by embossing the layer comprising the top sheet, second sheet and absorbent body.

[J9]

The absorbent article according to any one of J1 to J8, wherein the blood slipping agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;

with the proviso that when 2 or more oxy groups are inserted in the compound of (ii) or (iii), the oxy groups are not adjacent.

[J10]

The absorbent article according to any one of J1 to J9, wherein the blood slipping agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;

with the proviso that when 2 or more same or different bonds are inserted in a compound of (ii') or (iii'), the bonds are not adjacent.

[J11]

The absorbent article according to any one of J1 to J10, wherein the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of ($C_1$) a carboxylic acid, hydroxy acid, alkoxy acid or oxoacid comprising a chain hydrocarbon moiety and 2-4 carboxyl groups substituting for hydrogens on the chain hydrocarbon moiety, and ($C_2$) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

[J12]

The absorbent article according to any one of J1 to J11, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycols and at least one fatty acid, ($e_3$) an ether of a polyoxy $C_3$-$C_6$ alkylene glycol and at least one aliphatic monohydric alcohol, and ($f_1$) a chain alkane, and any combination thereof.

[J13]

The absorbent article according to any one of J1 to J12, wherein the blood slipping agent is attached to the surfaces of the fibers of the nonwoven fabric or woven fabric.

[J14]

The absorbent article according to any one of J1 to J13, wherein the absorbent article is a sanitary napkin or panty liner.

REFERENCES SIGNS LIST

1 Sanitary napkin
2 Top sheet
3 Absorbent body
4 Excretory opening contact region
5 Embossed section
6 Additional embossed section
7 Discontinuous section
8 Second embossed section

The invention claimed is:

1. An absorbent article comprising a liquid-permeable top sheet, formed from a nonwoven fabric or woven fabric, a liquid-impermeable back sheet, and an absorbent body between the top sheet and the back sheet,
wherein
the absorbent article has
an excretory opening contact region configured to contact with an excretory opening of a wearer, and
an embossed section which is continuously or discontinuously disposed and which surrounds the excretory opening contact region,
the embossed section includes the top sheet and the absorbent body,
the top sheet within the excretory opening contact region and the embossed section each comprise a blood slipping agent that has a kinematic viscosity of 0.01 to 80 mm$^2$/s at 40° C., a water holding percentage of 0.01 to 4.0 mass % and a weight-average molecular weight of less than 1000, and
a basis weight of the blood slipping agent in the embossed section is greater than a basis weight of the blood slipping agent in the top sheet within the excretory opening contact region.

2. The absorbent article according to claim 1, wherein the blood slipping agent further has an inorganic organic balance of 0.00-0.60.

3. The absorbent article according to claim 1, wherein
the embossed section is discontinuously disposed and surrounds the excretory opening contact region, and
the absorbent article further comprises one or more additional embossed sections disposed on outer sides of the embossed section.

4. The absorbent article according to claim 3, wherein
the embossed section includes discontinuous portions, and
the one or more additional embossed sections are disposed on the outer sides of the discontinuous portions of the embossed section.

5. The absorbent article according to claim 3, wherein
the one or more additional embossed sections comprise the blood slipping agent, and
a basis weight of the blood slipping agent in the one or more additional embossed sections is greater than the basis weight of the blood slipping agent in the top sheet within the excretory opening contact region.

6. The absorbent article according to claim 1, wherein the absorbent article further comprises a second embossed section disposed on an outer side of the excretory opening contact region in a lengthwise direction of the absorbent article, and the second embossed section includes the top sheet and the absorbent body.

7. The absorbent article according to claim 6, wherein the second embossed section is curved so as to surround an edge of the excretory opening contact region in the lengthwise direction.

8. The absorbent article according to claim 1, further comprising a second sheet between the top sheet and the absorbent body, wherein the embossed section includes the top sheet, the second sheet and the absorbent body.

9. The absorbent article according to claim 1, wherein the blood slipping agent is selected from the group consisting of following items (i)-(iii), and any combination thereof:
(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;
with the proviso that when 2 or more oxy groups are inserted in the compound of (ii) or (iii), the oxy groups are not adjacent.

10. The absorbent article according to claim 1, wherein the blood slipping agent is selected from the group consisting of following items (i')-(iii'), and any combination thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;
with the proviso that when 2 or more same or different bonds are inserted in a compound of (ii') or (iii'), the bonds are not adjacent.

11. The absorbent article according to claim 1, wherein the blood slipping agent is selected from the group consisting of following items (A)-(F), and any combination thereof:
(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;
(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;
(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;
(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;
(E) a polyoxy $C_3$-$C_6$ alkylene glycol, or alkyl ester or alkyl ether thereof; and
(F) a chain hydrocarbon.

12. The absorbent article according to claim 1, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycols and at least one fatty acid, ($e_3$) an ether of a polyoxy $C_3$-$C_6$ alkylene glycol and at least one aliphatic monohydric alcohol, and ($f_1$) a chain alkane, and any combination thereof.

13. The absorbent article according to claim 1, wherein the blood slipping agent is attached to surfaces of fibers of the nonwoven fabric or woven fabric.

14. The absorbent article according to claim 1, wherein the absorbent article is a sanitary napkin or panty liner.

* * * * *